(12) United States Patent
Tamura et al.

(10) Patent No.: US 7,341,691 B2
(45) Date of Patent: *Mar. 11, 2008

(54) AUTOMATIC ANALYZING APPARATUS

(75) Inventors: Tomoaki Tamura, Mishima (JP);
Hiroyuki Onishi, Shizuoka Pref. (JP);
Takayuki Mizutani, Mishima (JP)

(73) Assignee: Olympus Corporation, Tokyo (JP)

(*) Notice: Subject to any disclaimer, the term of this patent is extended or adjusted under 35 U.S.C. 154(b) by 612 days.

This patent is subject to a terminal disclaimer.

(21) Appl. No.: 10/242,257

(22) Filed: Sep. 12, 2002

(65) Prior Publication Data

US 2003/0049171 A1    Mar. 13, 2003

(30) Foreign Application Priority Data

Sep. 13, 2001    (JP) .............................. 2001-277740

(51) Int. Cl.
*G01N 21/00*    (2006.01)
(52) U.S. Cl. .......................... 422/64; 422/63; 422/65; 422/99; 422/100; 422/101; 436/180
(58) Field of Classification Search ................. 436/43, 436/45, 47, 180; 422/63–65, 99–101
See application file for complete search history.

(56) References Cited

U.S. PATENT DOCUMENTS

| | | | | |
|---|---|---|---|---|
| 4,647,432 | A | * | 3/1987 | Wakatake .................. 422/64 |
| 5,538,849 | A | * | 7/1996 | Uematsu et al. ............... 435/6 |
| 5,635,364 | A | * | 6/1997 | Clark et al. ................ 435/7.92 |
| 5,698,450 | A | | 12/1997 | Ringrose et al. |
| 2003/0049170 | A1 | * | 3/2003 | Tamura et al. ............... 422/63 |

FOREIGN PATENT DOCUMENTS

| | | |
|---|---|---|
| EP | 1 293 781 A2 | 3/2003 |
| JP | 5-80059 | 3/1993 |
| JP | 6-82461 | 3/1994 |
| JP | 7-49350 | 2/1995 |
| JP | 8-194004 | 7/1996 |
| JP | 10-19901 | 1/1998 |
| JP | 11-316235 | 11/1999 |
| WO | WO 99/57561 | 11/1999 |

OTHER PUBLICATIONS

Patent Abstracts of Japan for Japanese Publication No. 61118662, published Jun. 5, 1986.

* cited by examiner

*Primary Examiner*—Jill Warden
*Assistant Examiner*—Jyoti Nagpaul
(74) *Attorney, Agent, or Firm*—Scully, Scott, Murphy & Presser, P.C.

(57) ABSTRACT

An automatic analyzing apparatus for measuring an object substance in a specimen includes a reaction portion for causing the substance and a reagent commensurate thereto to react on each other, a detecting portion for detecting a signal or reaction condition from the reagent for measuring the object substance, and a cleaning portion for removing the substance of the specimen or unreacted substance in the reagent or cleaning the reacted liquids which have completed the reaction. The reaction, detecting and cleaning portions are independently arranged in a single frame provided in the apparatus. The apparatus further includes a transfer portion for transferring reaction vessels in succession between the reaction, detecting and cleaning portions. With this arrangement, the automatic analyzing apparatus achieves the high speed analyzing treatment and compact construction of the apparatus.

3 Claims, 13 Drawing Sheets

AUTOMATIC ANALYZING APPARATUS

BACKGROUND OF THE INVENTION

This invention relates to an automatic analyzing apparatus for measuring or detecting object substances in specimens such as immunity analysis utilizing the reaction between antigen and antibody, and chemicobiological analysis and the like, which is intended to perform the analyzing treatment at high speed and to make compact the apparatus itself.

A hitherto used automatic analyzing apparatus for measuring object substances in specimens fundamentally comprises, in an exemplary apparatus for immunity analysis, a reaction portion for causing a specimen substance to act on a reagent commensurate therewith in a reaction vessel, a detecting portion for detecting signals derived from the reagent, and a cleaning portion for removing the specimen substance or unreacted reagent or cleaning reaction liquid which has completed its reaction, these reaction, detecting and cleaning portions being arranged on a line or on turn tables.

FIG. 13 illustrates an exemplary analyzing apparatus of the prior art for measuring object substances on one line. With this apparatus, first a reaction vessel is transferred from a stocking portion 50 for storing reaction vessels onto a line 52 by means of a transfer unit 51. A sample collected from a sample rack 53 is dispensed into the reaction vessel located on the line 52 by a dispenser 54, and a reagent is dispensed from a reagent storage portion 55 into the reaction vessel by means of a dispenser 56.

After the lapse of a constant reaction time, the reaction vessel is subjected to a cleaning treatment (BF separation) at a cleaning portion 57 and a marker reagent is dispensed from a reagent storage portion 58 into the cleaned vessel by means of a dispenser 59, and after the lapse of a constant reaction time the reaction vessel is again subjected to a cleaning treatment at a cleaning portion 60.

After termination of the cleaning treatment, a reagent is dispensed into the reaction vessel in a light-emission reagent storage portion 61, and after the lapse of a constant reaction time, the reaction vessel is located at a light measuring portion 62. After the termination of the measurement, the reaction vessel is transferred to a discarding position 64 by a transfer portion 63.

With such an automatic analyzing apparatus of the prior art, however, as the treating capacity of the apparatus increases, the processing line problematically becomes lengthy (in case of turn tables, their diameters become large). Such a problem is particularly acute in an apparatus as shown in FIG. 14 whose processes include pretreatment and predilution (which means such a dilution to be previously performed preparatory to a next step).

In connection therewith, there is a procedure which uses reaction plates capable of simultaneously treating a plurality of specimens to perform measurements by transferring specimens and reagents to respective exclusive ports with the aid of these plates in reaction, cleaning and detecting processes. With such a procedure, however, treatments are carried out after samples have accumulated to predetermined amounts, which is a so-called "batch processing" different from the "real time processing". It is, therefore, impossible to increase the speed in treatment and to control reaction times for measurements, so that it is difficult to perform the treatments at higher speeds (to shorten the lead time).

In case of measuring immunity items employing the reaction in the heterogeneous method (for example, two step sandwich method), cleaning after first reaction and also cleaning after second reaction are needed. In case of performing cleaning operations at reaction portions, it is required to provide, for example, magnets for magnetically collecting magnetic particles used as carriers in measurement system and further two cleaning units so that such an apparatus would become complicated. In addition, because of movements of the reaction portions required for dispensation of reagents, it would be difficult to provide the sufficient time for the magnetic collection of magnetic particles described above and the time for the cleaning.

SUMMARY OF THE INVENTION

It is an object of the invention to provide an improved automatic analyzing apparatus which overcomes all the disadvantages of the prior art and which can attain high speed treatment and miniaturization of the apparatus and in addition can accomplish reduction in manufacturing cost and improvement in reliability of data by making units participating reactions usable as in common as possible.

In order to achieve the object of the invention, the automatic analyzing apparatus for measuring an object substance in a specimen according to the invention comprises a reaction portion for causing said substance of the specimen and a reagent commensurate thereto to react on each other, a detecting portion for detecting a signal or reaction condition from said reagent for measuring the object substance, and a cleaning portion for removing said substance of the specimen or unreacted substance in said reagent or cleaning the reacted liquids which have completed the reaction, and said reaction, detecting and cleaning portions being independently arranged in a single frame, and a transfer portion being provided for transferring reaction vessels in succession between said reaction, detecting and cleaning portions to perform said measurement of the object substance.

In the automatic analyzing apparatus according to the invention, preferably the reaction, detecting and cleaning portions are in the form of turn tables, respectively. The reaction portion may have sections for carrying out pretreatment and dilution of specimen.

The cleaning portion preferably has a function for magnetically collecting magnetic particles and an agitating function for dispersing magnetic particles. The detecting portion is arranged to be divided into a detecting reaction portion and a detecting measurement portion.

According to the invention the automatic analyzing apparatus is arranged in a device or in a single frame so as to permit the reaction, detecting and cleaning portions to be independently arranged to have respective ports, thereby reducing dead spaces in the apparatus.

The reaction, detecting and cleaning portions are made in the form of turn tables to shorten the moving distances of nozzles used in dispensing samples and reagents and cleaning to the minimum distances, to simplify the control concerning with measurement, to improve accuracy and reliability and to reduce manufacturing cost. Moreover, transferring distances of reaction vessels between the tables become shorter so that it is possible to improve the reliability and to reduce the manufacturing cost. The reaction time can be severely determined correspondingly to the movement of the tables, thereby improving the accuracy of measured data. In this case, the respective tables can be smaller so that temperature control can be easily performed.

By previously providing a pretreatment port and a dilution port in reaction portion, the reaction portion can be smaller which would otherwise be bulky, thereby enabling application to pretreatment items that would otherwise be impossible.

Assuming that the apparatus is used in measurement of immunity items whose magnetic material is solidus carrier (magnetic particle carriers), there are provided a magnetically collecting function such as a magnet for magnetically collecting the magnetic particle carriers, and an agitating function for dispersing the magnetic particle carriers. By making the cleaning portion independent, it is possible to gather members required in the case using for immunity items as magnetic particle carriers together into one. Such members are, for example, the magnets (magnets for magnetically collecting magnetic particle carriers), agitating function and cleaning nozzles, which would otherwise be plural after first reaction and after second reaction, respectively. Therefore, it serves to reduce the manufacturing cost. In this case, the number of nozzles to be used can be reduced so that difference in cleaning performance between nozzles separately produced can be smaller to improve the reliability of measured data.

Assuming that weak light-emission is detected at the detecting portion, a detecting measurement portion completely shut off from light is previously provided separately from the detecting reaction portion so that even weak light-emission reaction can be measured with high accuracy and high sensitivity, thereby enabling detection by fluorescence and chemical light-emission as well as the prior art calorimetric detection.

According to the invention the reaction vessels themselves are transferred between the respective portions. At that time, a monitoring function can be added for securely monitoring the transferring state of the reaction vessels. By transferring the reaction vessels themselves as described above, cleaning of nozzles for transferring liquids to be inspected and cleaning of reaction vessels after respective reactions (cleaning of reaction vessels after transferring of liquids to be inspected) can be dispensed with. Moreover, it is possible to prevent incorrect data due to insufficient cleaning and to reduce running cost by reducing the washing operation. Disposable reaction vessels can be used so that the contamination of reaction vessels that is not allowed in immunity analysis can be avoided, and the reduction of washing mechanism for reaction vessels serves to improve the reliability of data and to miniaturize the apparatus.

Means for detecting whether reaction vessels have been exactly transferred may be provided in the transfer mechanism. Such means do not affect the size of the apparatus.

According to the invention, the reaction, detecting and cleaning portions and reagent storage portion can be arranged on a locus through which a dispensing nozzle passes so that only one dispensing nozzle unit can be sufficiently used different from the prior art requiring a plurality of dispensing nozzle units.

According to the invention it is possible to provide an automatic analyzing apparatus which accomplishes the high speed treatment and the miniaturization of the apparatus itself, and is expensive to manufacture, wieldy or easy to use and high in reliability including reliability of measured data.

The invention will be more fully understood by referring to the following detailed specification and claims taken in connection with the appended drawings.

BRIEF DESCRIPTION OF THE DRAWINGS

FIG. 5b is a side view of the reaction vessel transfer portion shown in FIG. 5a;

DESCRIPTION OF THE PREFERRED EMBODIMENTS

Figure 1:
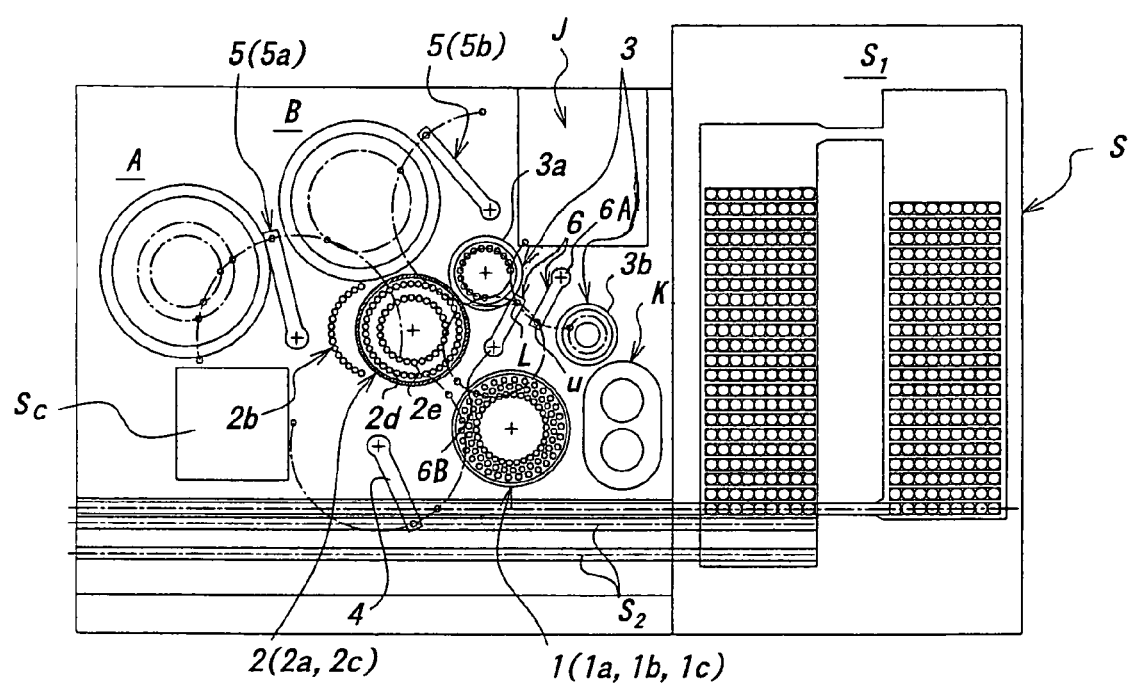
FIG. 1 is a view illustrating the entire construction of the automatic analyzing apparatus according to the invention.
Figure 2:
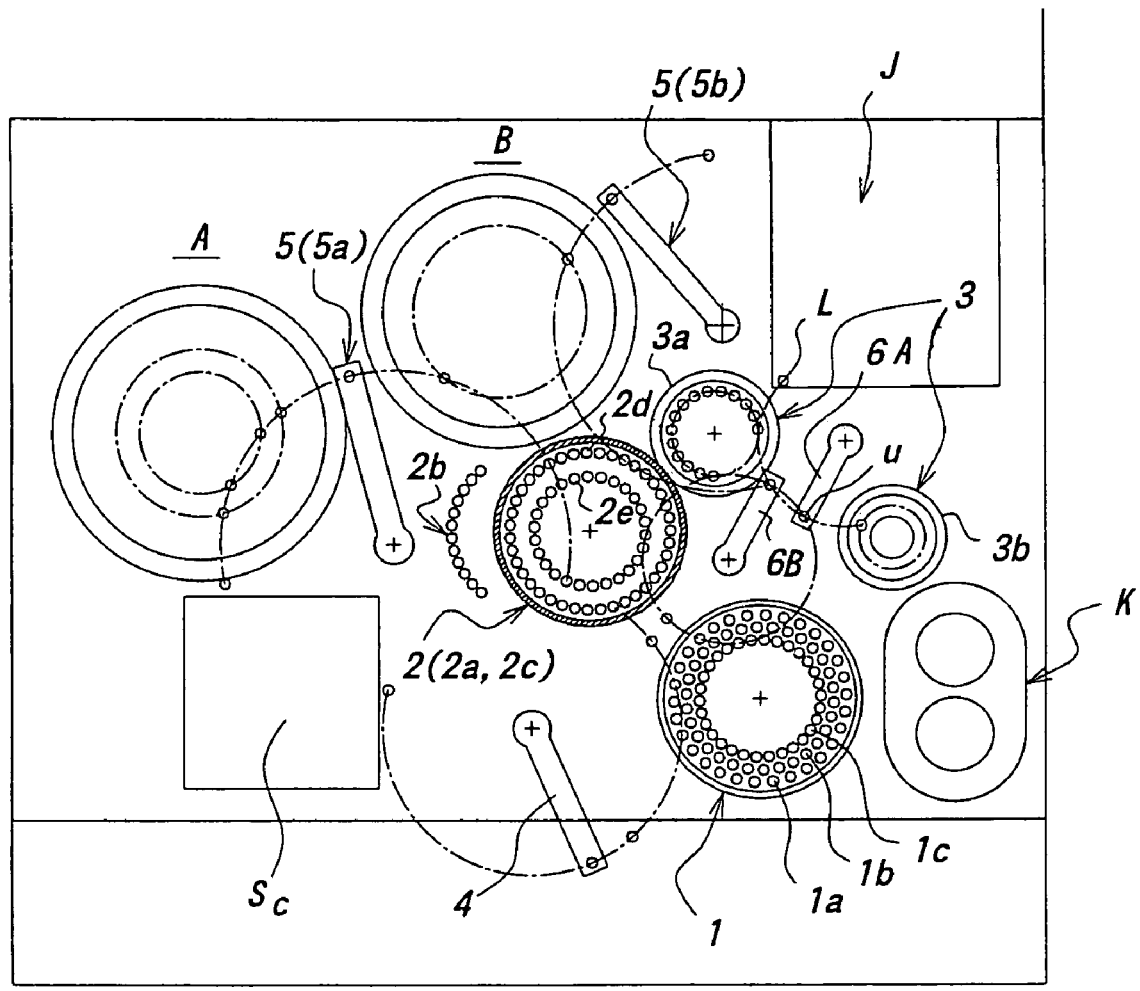
FIG. 2 is a view illustrating an important part (analyzer) of the apparatus shown in FIG. 1.

The present invention will be concretely explained in more detail with reference to the drawings hereinafter. FIG. 1 illustrates the entire construction of an automatic analyzing apparatus for immunity measurement based on chemical light-emission detection using magnetic particle carriers as solidus carriers, to which the automatic analyzing apparatus according to the invention is applied. FIG. 2 shows an important part of the apparatus shown in FIG. 1.

In FIGS. 1 and 2, the automatic analyzing apparatus comprises a immunity reaction portion (referred to hereinafter as "immunity reaction table") 1, which may have a configuration of triple construction dividing its reaction line into outer, intermediate and inner circumferential lines 1a, 1b and 1c. The outer circumferential line 1a is used for pretreatment and predilution and the intermediate circumferential line 1b is for immunity reaction between samples and solidus carrier reagents. The inner circumferential line 1c is for immunity reaction between sample-solidus carrier immunity composite material and marker reagent combined with marker substance for producing signals.

The automatic analyzing apparatus further comprises a cleaning portion (referred to hereinafter as "BF table") 2 which has a magnetically collecting mechanism (magnet) 2a for magnetically collecting magnetic particle carriers required for BF (bound-free) separation, BF cleaning nozzles $2b$ for carrying out the BF separation, and an agitating mechanism $2c$ for dispersing the magnetically collected carriers.

In the BF table 2, the magnetically collecting step, the cleaning step and the dispersing step are effected in succession correspondingly to the rotation of the BF table 2. The BF-cleaning nozzles $2b$ have a particular function that prevent the nozzles $2b$ from entering the reaction vessels or reactors in case of inspection items which need no BF separation.

For the dispersing step described above, it is required that reagents have been previously dispensed in the reaction vessels. Therefore, reagent storage portions A and B are arranged adjacent the BF table 2 so that all the dispensations of reagents take place at the BF table 2.

In the illustrated embodiment, the BF table 2 is constructed in double lines, that is, outer and inner lines, the former being the dispensing line $2d$ for the reagent which reacts on a sample, and the latter being the dispensing line $2e$ of the reagent after the BF separation. With this arrangement, it is possible to perform the dispensations with an improved efficiency. In dispensing a reagent for reacting on a sample having nothing to do with the BF separation, moreover, no magnetic collection mechanism is applied, without collecting magnetic particle carriers, so that the reaction between the sample and the reagent is caused to proceed with high efficiency immediately after the sample dispensation.

It is envisioned that the suction and discharge agitation can be used for the agitating step. In the present invention, however, the agitating system can be employed, in which agitation is carried out by bringing agitating elements into contact with the reaction vessel or reactor.

Figure 3:
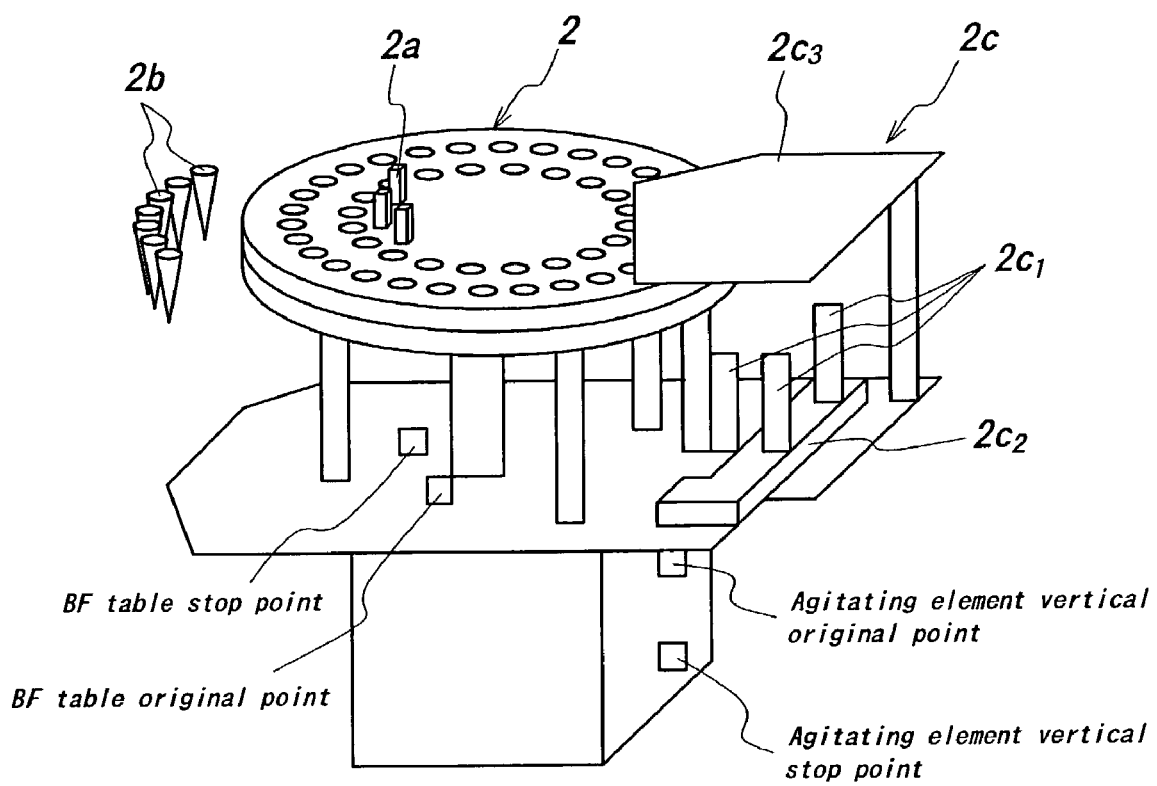
FIG. 3 is a view pictorially illustrating the agitating mechanism of the analyzing apparatus according to the invention.

In the case, for example, that there are a plurality of locations required to be agitated at a time, it is possible to use the agitating mechanism $2c$ provided with a plurality of agitating elements as shown in FIG. 3. By operating driving source of such an agitating mechanism $2c$, it is possible to agitate at a plurality of locations at a time.

In FIG. 3, the agitating mechanism $2c$ comprises agitating elements $2c_1$, a driving source (for example, an electric motor or the like) $2c_2$ for rotating the agitating elements $2c_1$, and a restraining member $2c_3$ for restraining the agitating elements $2c_1$ when being agitated.

By the rotation of the BF table 2, the magnetic particles in the reaction vessels are magnetically collected and cleaned in this state by means of the BF nozzles $2b$. Thereafter, when the reaction vessels have arrived at the position of the agitating mechanism $2c$, the contents in the reaction vessels are agitated by the agitating mechanism $2c$ so as to permit the magnetic particle carriers in the reaction vessels are dispersed. The agitating elements $2c_1$ are arranged on the driving source $2c_2$ which is vertically movable with the aid of a further driving system (not shown).

In agitating, the driving source $2c_2$ is moved upward to bring the agitating elements $2c_1$ into contact with the bottoms of the reaction vessels and the restraining member $2c_3$ is urged against the upper surfaces of the reaction vessels so that the reaction vessels are embraced between the agitating elements $2c_1$ and the restraining member $2c_3$. The agitating elements $2c_1$ are rotated by the driving source $2c_2$ to rock the reaction vessels, thereby agitating the contents in the reaction vessels. In this case, it is desirable to fix the reaction vessels by means of the restraining member $2c_3$ to prevent the reaction vessels from irregularly jumping out of their fixed positions to permit their contents to splash.

With the agitating mechanism $2c$ described above, it is possible to perform the dispersion of magnetic particle carriers and the mixture of the sample and reagent in the same unit, so that the miniaturization of the apparatus and the reduction in its manufacturing cost can be accomplished.

The apparatus shown in FIGS. 1 and 2 further comprises detecting reaction tables 3 which form a reaction line for producing signals from the immunity composite material combined with the marker substance. The marker substance is for producing signals and may be, for example, an enzyme to which a substrate liquid in a substrate liquid storage portion K is added to produce the signals.

If the signals are of variation in color, it may be possible to provide a colorimetric detector in the reaction line. In case of using light-emission detection based on the chemical light-emission method, however, because of a need for reducing noise due to stray light as much as possible, there are provided in the reaction line a detecting reaction portion $3a$ and a detecting measurement portion $3b$ for detecting the signals. The detecting measurement portion $3b$ is for detecting weak light-emission produced in the chemical light-emission. In more detail, a photomultiplier tube is used to count the amount of light emission.

In order to obtain a dynamic range for the light-emission measurement, an optical filter is provided at a location of the light-emission measurement portion to measure the light reduced by the filter depending upon the intensity of light-emission, thereby calculating the value of real light-emission from the reduced measured value.

The apparatus further comprises a sample dispensation transfer portion 4 which is actually a sample dispensing nozzle which serves to collect specimens from racks supplied by a sampler S to dispense them into required reaction vessels. In case of items requiring dilution and pretreatment, for example, the specimens are dispensed into reaction vessels on the outer circumferential line $1a$ of the immunity reaction table 1, that is, into the reaction vessels on the line for the pretreatment and predilution. In case of a usual analysis not requiring the pretreatment and predilution, the specimens are dispensed into reaction vessels which have reagents previously dispensed at the BF table 2.

The sampler S consists of a rack storage portion $S_1$ for racks having specimens therein and a rack transfer portion $S_2$ for transferring the racks received in the rack storage portion $S_1$ in succession to sample dispensing positions by means of the rack transfer portion $S_2$. The racks include general specimen racks, quality control racks, measurement line racks, emergency measurement racks, or reinspection racks (racks for second inspection). The sampler S has a function which can distinguish these racks, thereby enabling the apparatus to perform analysis to meet the purposes of the racks. Moreover, the racks can be located at respective exclusive positions, and if required, exclusive racks can be preferentially transferred.

In the case that the respective racks have exclusively located positions, they may be preferentially transferred from those positions, and positions at which racks are to be set may be provided in a manner to enable the racks to be newly set. Moreover, a distinguishing function may be provided so that the relevant racks in the sampler S are found out by the distinguishing function and then transferred. Other than the rack distinguishing function, the sampler S has a function that is able to recognize information codes representative of bar codes attached to racks and samples. Analyzing operations may be determined depending upon this function.

The dispensation of samples may be effected by means of fixed nozzles. In consideration of carry-over that is undesirable but occurs in measurement of infection items, disposable sample tips are fitted on distal ends of sample dispensing nozzles to perform dispensation and after use the sample tips are exchanged with new ones.

Figure 4:
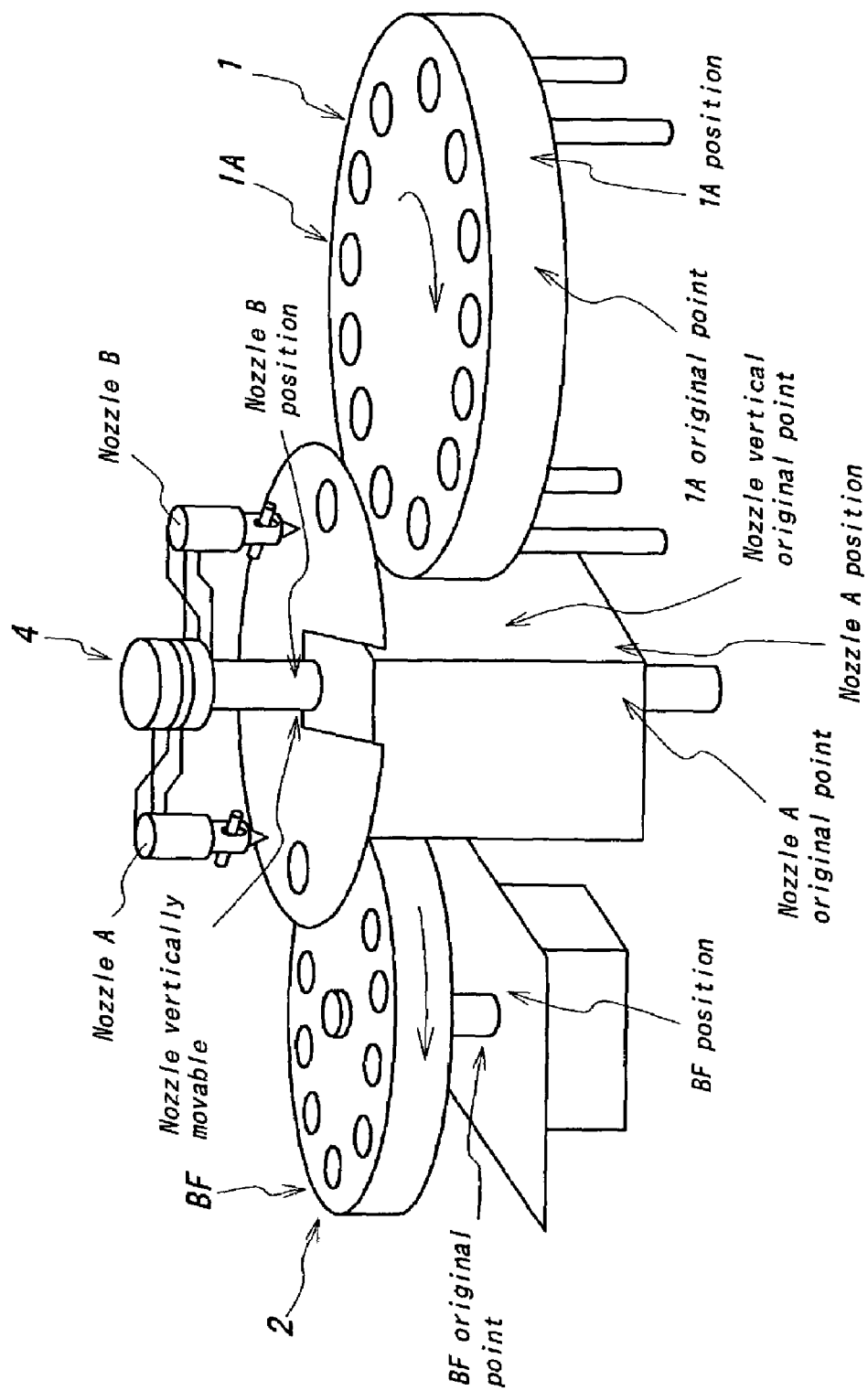
FIG. 4 is a perspective view showing the outline of the sample dispensation transfer portion of the automatic analyzing apparatus according to the invention.

The sample dispensation transfer portion 4 is designed in a manner to form an operating locus passing through a sample tip supply unit Sc, the rack transfer portion $S_2$ of the sampler S, the immunity reaction table 1, and the BF table 2 so that there is no need for preparing a plurality of sample dispensation transfer portions corresponding to inspection items. FIG. 4 is a perspective view showing the outline of the sample dispensation transfer portion 4.

The apparatus further comprises a reagent dispensation transfer portion 5 as shown in FIG. 1 which is actually a reagent dispensing nozzle for collecting reagents from reagent bottles arranged in the reagent storage portions A and B.

Reagents are dispensed by the reagent dispensation transfer portion 5 into reaction vessels immediately after they have been cleaned by the BF cleaning at the BF table 2 or into reaction vessels in which samples have not been dispensed.

The reagent dispensation transfer portion 5 is designed in a manner to form an operating locus passing through the reagent storage portions A and B, the BF table 2, and a reaction vessel supply and transfer portion to be described later so that there is no need for preparing a plurality of reaction vessel supply and transfer portions.

According to the exemplary embodiment of the invention, in order to make the treating speed higher, the number of the units of the reagent dispensation transfer portion 5 is two, that is, reagent dispensation transfer portions 5a and 5b so that it is possible to receive and dispense the reagents at a plurality of locations.

The BF cleaning nozzle 2b is for sucking the inspection liquids or BF liquids and supplying BF liquids and is formed by a suction nozzle and a delivery nozzle forming one set of BF cleaning nozzles.

In FIGS. 1 and 2, the apparatus further comprises a reaction vessel transfer portion 6 for transferring the reaction vessels between the respective tables and further transferring the reaction vessels to a reaction vessel supply portion U, the detecting reaction portion 3a, the detecting measurement portion 3b, and a reaction vessel disposing portion L. The reaction vessel transfer portion 6 may be constructed by vessel gripping means or the transfer portion 6 may be means for inserting a transfer probe into a reaction vessel.

Figure 5A:
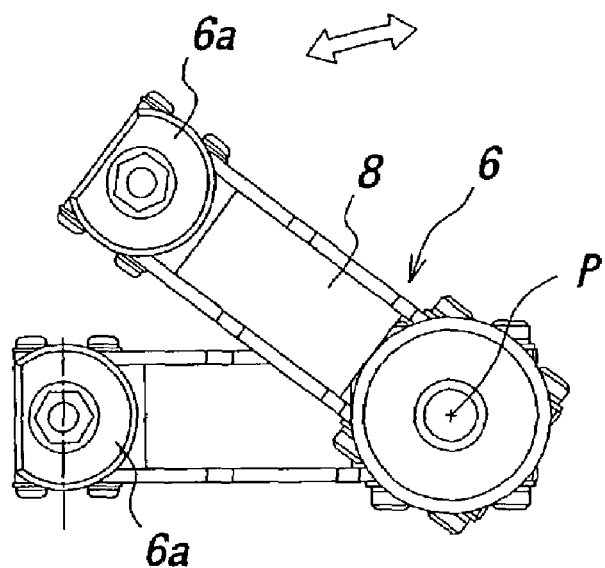
FIG. 5a is a plan view illustrating the reaction vessel transfer portion of the automatic analyzing apparatus according to the invention.
Figure 5B:
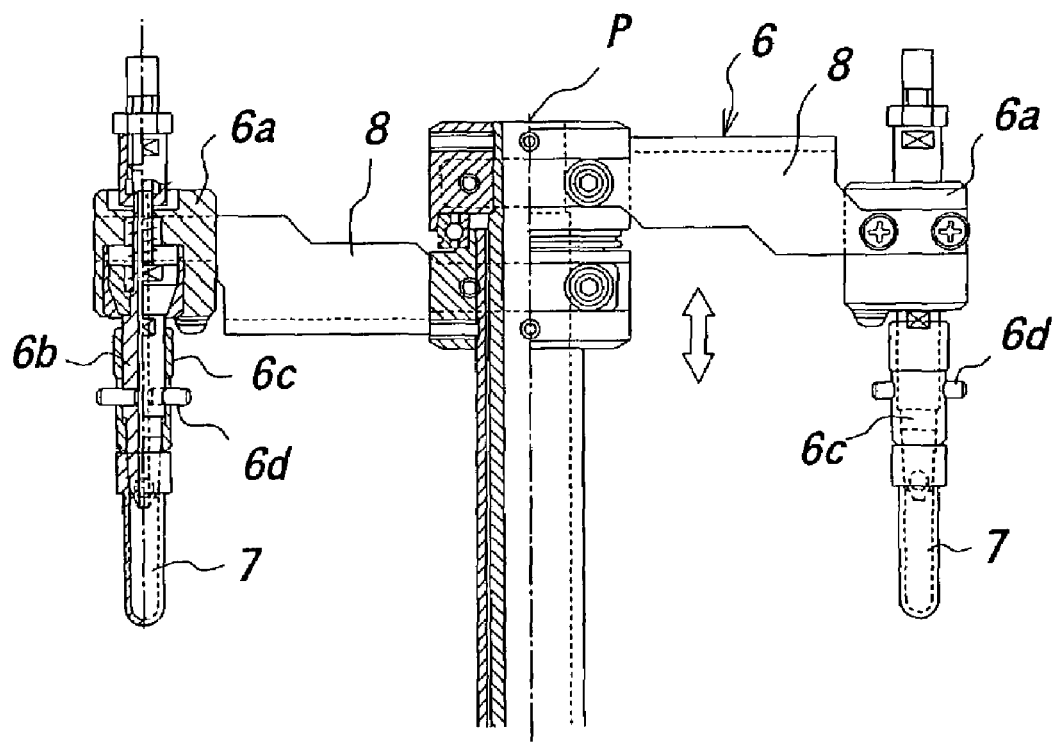

FIGS. 5a and 5b schematically illustrate the construction of the reaction vessel transfer portion 6. A reference numeral 7 in the drawings denotes reaction vessels to be transferred. The reaction vessel transfer portion 6 comprises a transfer portion 6a, a rod portion 6b for supporting the reaction vessel 7 fitted therewith through insertion, and a guide portion 6c surrounding the rod portion 6b thereabout and movable therealong. The rod portion 6b is provided with protrusions 6d as stoppers regulating the movement of the guide portion 6c. The reaction vessel transfer portion 6 is supported by an arm 8 which is vertically and pivotally movable about the axis P.

Figure 6:
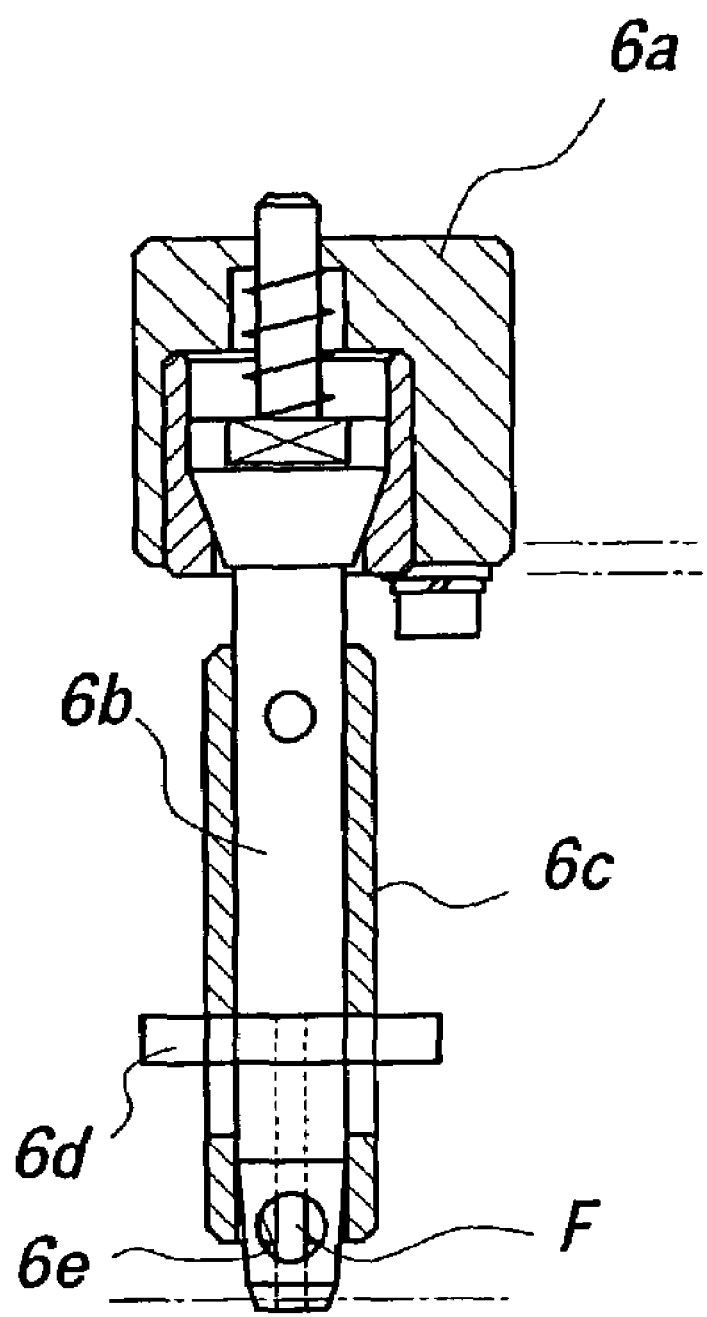
FIG. 6 is a view illustrating the transfer portion before mounting a reaction vessel used in the automatic analyzing apparatus according to the invention.
Figure 7:
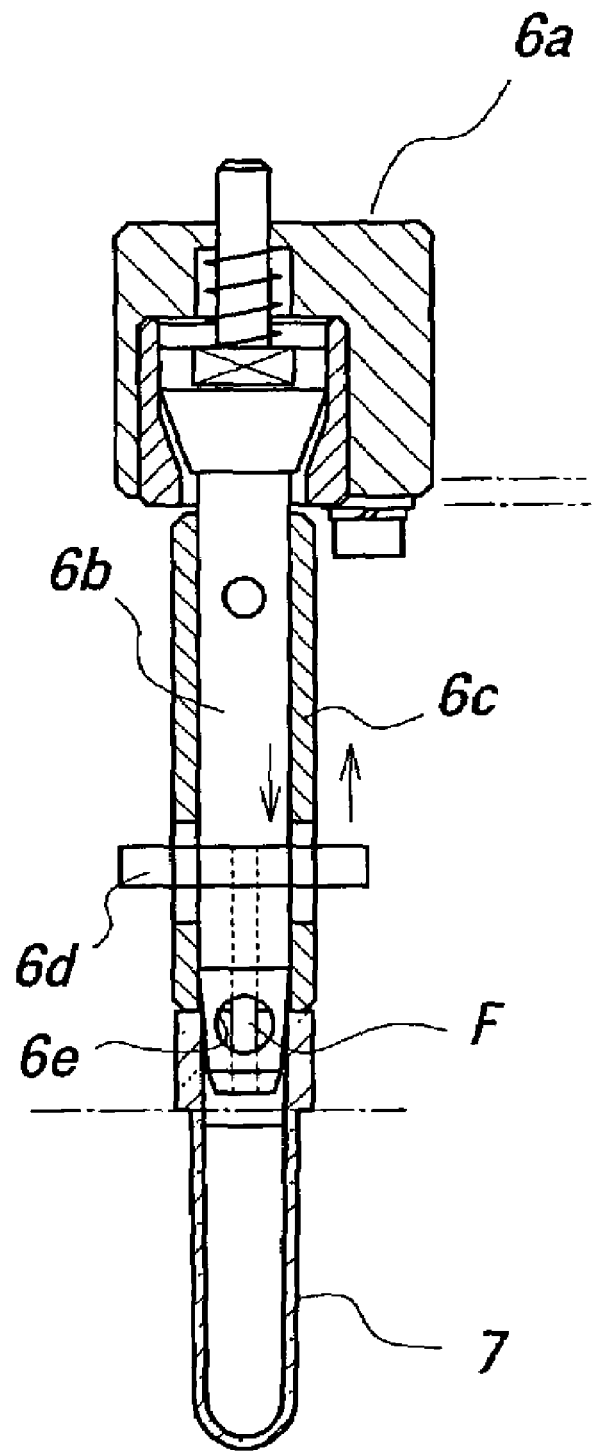
FIG. 7 is a view showing the transfer portion shown in FIG. 6 together with a reaction vessel mounted thereon.

FIG. 6 illustrates the reaction vessel transfer portion 6 before a reaction vessel 7 has been fitted therewith and FIG. 7 shows after the reaction vessel 7 has been fitted. The guide portion 6c is freely movable between the reaction vessel 7 and the transfer portion 6a as shown in FIG. 7.

Figure 8:
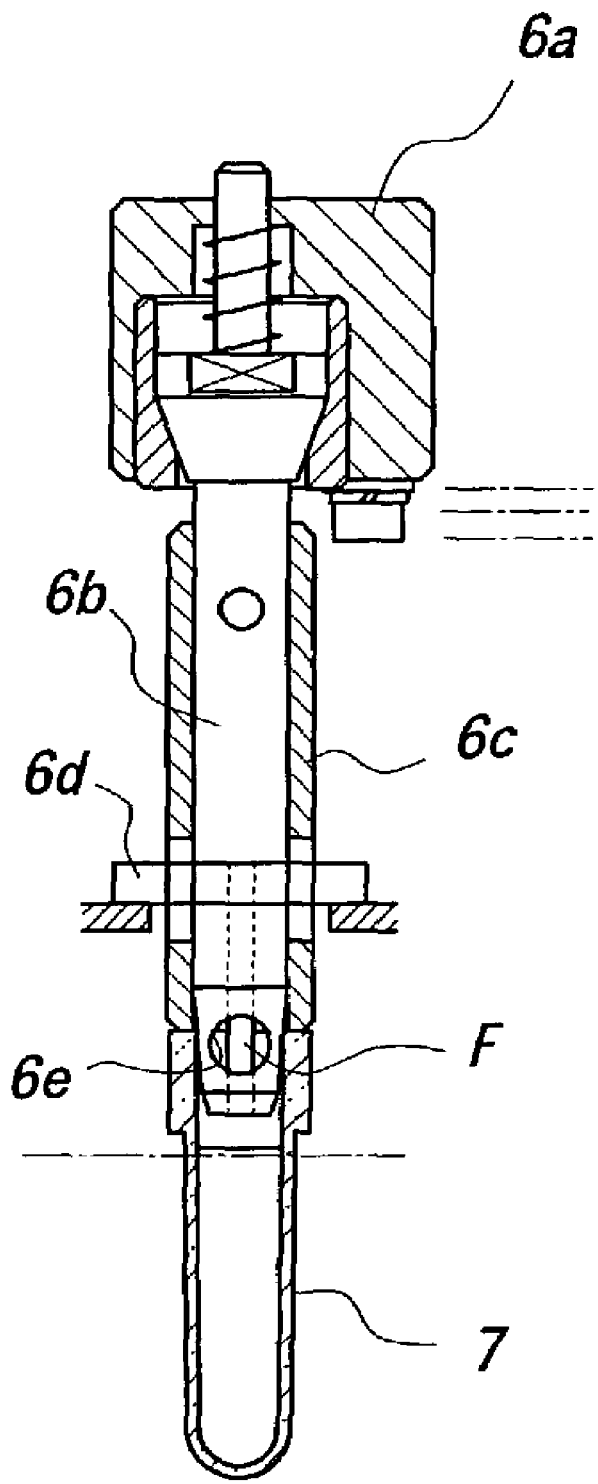
FIG. 8 is a view showing the transfer portion shown in FIG. 7 for explaining the removal of the reaction vessel from the transfer portion.
Figure 9:
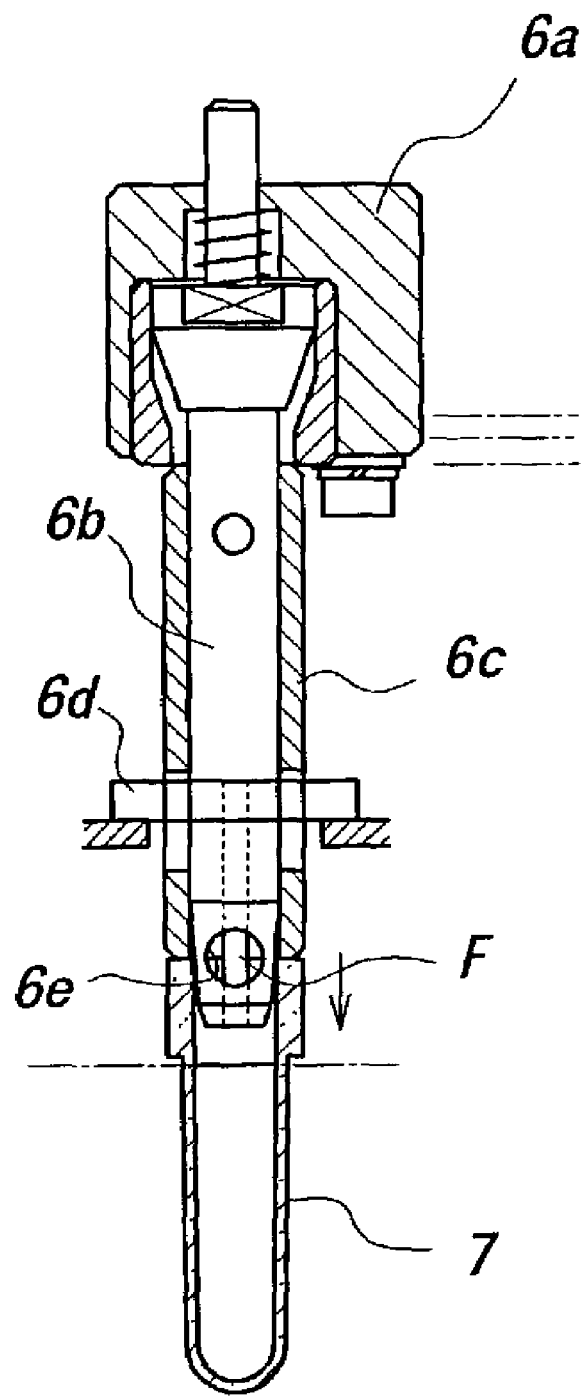
FIG. 9 is a view illustrating the transfer portion and the reaction vessel shown in FIG. 8 in the next step of removal of the reaction vessel.

FIG. 8 illustrates the reaction vessel transfer portion 6 before the reaction vessel 7 is removed. To remove the reaction vessel 7 from the rod portion 6b of the reaction vessel transfer portion 6 in the state shown in FIG. 8, the reaction vessel transfer portion 6 itself is fixed with the aid of the protrusions 6d and thereafter the transfer portion 6a is actuated to cause the guide portion 6c to urge the reaction vessel 7 downward.

With this arrangement, different from means for gripping the reaction vessel, one mechanism can be dispensed with so that it will contribute to the reduction in manufacturing cost and the improvement in reliability.

In transferring the reaction vessel 7, there is a need for a mechanism for detecting whether the reaction vessel 7 has been securely transferred. As such means, envisioned are a method for detecting a fitted state between the reaction vessel 7 and the rod portion 6b by the use of a piezo-electric element secured to the distal end of the rod portion 6b, and another method for detecting from outside of the transfer unit whether the reaction vessel 7 has been fitted with the rod portion 6b with the aid of an optical sensor. It is, however, particularly preferable to provide an optical detection sensor embedded in the rod portion 6b in order to realize the miniaturization and less manufacturing cost of the apparatus.

In reality, the rod portion 6b is formed at its distal end with windows 6e to which light is supplied from a light source located at the arm portion through an optical fiber F to detect a fitting condition of the reaction vessel 7 with the aid of the light reflection as shown in FIGS. 6 to 9. Such a detection is possible regardless of the positions of the arm so that it is not required to provide a plurality of sensors depending upon the positions of the arm.

The reagent storage portions A and B are kept at constant temperatures which are comparatively lower temperatures and may be arranged on the operating locus of reagent dispensation transfer portion 5 or may be constructed in the form of turn tables and arranged on the same operating locus.

In order to increase the number of settled reagents, according to the exemplary embodiment of the invention there are provided two reagent storage portions constructed as turn tables, and the reagent storage portions A and B are arranged on the operating locus of the reagent dispensation transfer portion 5, thereby enabling a single transfer portion to dispense reagents contained in a plurality of reagent storage portions.

In case of preparing two reagent storage portions for magnetic particle solidus carrier reagent liquid and for marker reagent, by providing such two reagent storage portions, where the respective reagents should be set can be clearly distinguishable. With this arrangement, moreover, it may be possible to vary shapes of reagent bottles depending upon the kinds of reagents to limit the places where the reagents are set by providing shaped portions to meet the shapes of the bottles.

The numbers of reagents permitted in the respective reagent storage portions may be not necessarily the same. Bearing in mind that the pretreatment liquids or dilute solutions are set in either of the reagent storage portions, for example, more of the reagents may be set in one of the reagent storage portions.

In the event that the reagents to be set in the reagent storage portions are, for example, magnetic particle solidus carrier reagents, the magnetic particles will settle out as the time elapsed to cause a concentration gradient, resulting in incorrect data.

In order to prevent such incorrect data, the reagents are agitated in the reagent dispensation transfer portion 5 before the dispensation of the reagents. For example, the liquids are agitated by suction and discharge agitation, or the magnetic particles are dispersed with the aid of an ultrasonic vibratory element provided on the nozzle.

For such a purpose, it is preferable to provide an agitating mechanism at the reagent storage portion for dispersing the magnetic particles. With this arrangement, the reagent previously received in a cylindrical bottle is subjected to rotation about an axis of the bottle so as to permit the magnetic particles to disperse with the aid of frictional force between the liquid and the wall surface of the bottle. Such rotation about the axis may be accomplished in connection with the rotation of the turn table so that a driving mechanism for the rotation of the bottle about its axis can be dispensed with.

In the case using the magnetic particle solidus carrier reagents as reagents, according to the invention it is possible to gather these reagents together in one reagent storage portion so that the agitating mechanism described above is needed only in one receiving portion to serve to reduce the manufacturing cost.

The agitating mechanism should not be limited to that described above. If the reagent storage portion is a turn table, for example, the turn table may be rotated at a high speed for utilizing the centrifugal force, or agitating elements are brought into abutment against the bottle to agitate the regent in the bottle.

A bottle of the reagent has a reagent code (for example, bar code) attached thereto recording the information of the reagent (for example, a lot, effective term, measurement line information or the like). The regent storage portion is provided with means for reading these codes (for example, a bar code reader, image reader, magnetic reader or the like) so that the information read from the information code together with positional information of the reagent storage portion which has been set, its set date and the like is transmitted to a data processor and memorized.

The substrate storage portion (substrate dispensing unit) K may be arranged in the proximity of the reagent storage portions A and B. In the present invention in consideration of the need for a large amount of reagent because the substrate is a common reagent, separate substrate receiving portions are preferably provided to dispense the reagent at exclusive dispensing units.

In reality, a plurality of bottles for receiving the substrate are made to be set simultaneously and the dispensation is effected by the line dispensing system. At this time, even if bottles concerning different lots are set, it is preferable to selectively dispense the reagent from the respective bottles, thereby enabling the dispensation from the needed bottles.

The sample tip supply unit Sc is provided on the apparatus with a tip case having a plurality of aligned tips, from which tip case the chips are supplied. In reality, the tip case may be moved to the tip supply positions, or tip transfer means may be used to transfer the tips from the tip case to the supply positions for supplying the tips. The tip case is longitudinally received so as to occupy a minimum possible space to miniaturize the apparatus.

Similarly to the sample tip supply unit Sc, with, the reaction vessel supply unit J, empty vessels 7 aligned on a box are arranged on the apparatus to transfer the box to the position of reaction vessel supply portion U. In consideration of addition of reactor vessels 7 at any time and miniaturization of the apparatus, feeders for parts are provided in the apparatus so as to be aligned at the position of the reaction vessel supply portion U.

An analyzing method for automatic analysis using two step method with the apparatus shown in FIG. 1 will be explained hereinafter. Reaction vessels 7 are supplied from the reaction vessel supply unit J and set on the reaction vessel supply portion U. The reaction vessels set on the reaction vessel supply portion U by means of the reaction vessel transfer portion 6A are then transferred to the cleaning table (outside) 2 by the reaction vessel transfer portion 6B, and thereafter the magnetic particle solidus carrier reagent is dispensed into the reaction vessels by the reagent dispensation transfer portion (dispensing nozzles) 5.

Samples are collected from the specimen racks supplied by the sampler S by means of the sample dispensation transfer portion 4 having disposable sample tips mounted thereon and are dispensed into reaction vessels 7 on the cleaning table. The contents in the reaction vessels 7 are then agitated by the agitating mechanism 2c of the BF table 2 and thereafter the reaction vessels 7 are transferred to the intermediate circumferential line 1b of the immunity reaction table 1 by means of the reaction vessel transfer portion 6B.

After the lapse of the constant reaction time, the reaction vessels 7 are further transferred to the BF table (inside) 2 by means of the reaction vessel transfer portion 6B, and the magnetic particle carriers in the reaction vessels are magnetically collected by means of the magnetically collecting mechanism 2a set on the BF table 2 and are subjected to the BF separation by the BF cleaning nozzles 2b.

After the BF separation, the marker reagents are dispensed from the reagent storage portion A into the reaction vessels 7 by means of the reagent dispensation transfer portion 5, and the contents in the reaction vessels are agitated by the agitating mechanism 2c. After the agitation, the reaction vessels 7 are transferred to the inner circumferential line 1c of the immunity reaction table 1 by means of the reaction vessel transfer portion 6B, and after the lapse of the constant reaction time, the reaction vessels 7 are transferred to the BF table (inside) 2 by means of the reaction vessel transfer portion 6B.

The magnetic particle carriers in the reaction vessels 7 are further magnetically collected by means of the magnetically collecting mechanism 2a and are subject to the BF separation by the BF cleaning nozzles 2b. After the BF separation, the substrate liquids in the substrate storage portion K are dispensed into the reaction vessels 7 by means of the substrate liquid dispensing unit.

After the dispensation of the substrate liquids, the contents in the reaction vessels are further agitated by the agitating mechanism 2c, and thereafter the reaction vessels are once located at the detecting reaction portion 3a of the detecting reaction table 3 by the reaction vessel transfer portion 6B. After the lapse of the constant reaction time, the reaction vessels are transferred to the detection measurement portion 3b by means of the reaction vessel transfer portion 6A, where the light emitted from the reaction vessels 7 is measured by the use of the photomultiplier tube to determine the existence of the object substance in the specimen to be inspected.

After the measurement described above, the reaction vessels 7 are transferred to the reaction vessel disposing position L by means of the reaction vessel transfer portion 6A and are disposed or thrown away.

The automatic analysis using one step method will be carried out in the following manner. First, the reaction vessels 7 are set in the reaction vessel support portion U by means of the reaction vessel transfer portion 6A and further transferred to the BF table (outside) 2 by means of the reaction vessel transfer portion 6B.

The magnetic particle solidus carrier reagents and marker reagents are dispensed into the reaction vessels 7 transferred to the BF table 2 by means of the reagent dispensation transfer portion 5. Samples are collected from the specimen racks supplied from the sampler S by means of the sample dispensation transfer portion 4 having sample tips fitted thereon and are dispensed into the reaction vessels 7 on the BF table 2.

After the contents in the reaction vessels 7 are agitated by the agitating mechanism 2c, the reaction vessels 7 are transferred to the intermediate circumferential line 1b of the immunity reaction table 1 by means of the reaction vessel transfer portion 6B, and after the lapse of a constant reaction time in the line 1b, the reaction vessels 7 are transferred to the BF table (inside) 2 by means of the reaction vessel transfer portion 6B.

The reaction vessels 7 described above set on the BF table 2 are subjected to the BF cleaning process and at that time, the BF cleaning nozzles 2b are controlled so as not to be transferred into the reaction vessels 7 so that the BF separation does not take place.

It can be thought that the reaction vessels 7 may be affected by the influence of the magnetic collecting mechanism 2a. Similarly to the two step method, therefore, the contents in the reaction vessels are agitated by the agitating mechanism 2c on the BF table 2, and the reaction vessels are then transferred to the inner circumferential line 1c of the immunity reaction table 1 by means of the reaction vessel transfer portion 6B. Thereafter, the same steps as those in the two step method are carried out to determine the existence of the object substances.

Moreover, the present invention can perform an analysis in a manner to combine the one and two step methods. For example, the invention is applicable to a reaction system in that a sample and a marker reagent are caused to react on each other and magnetic particle carrier reagent is dispensed into a reaction vessel 7 without carrying out the BF separation (delay one step method).

The automatic analysis using two step method including dilution and pretreatment is performed in the following manner. Reaction vessels (for dilution and pretreatment) 7 supplied from the reaction vessel supply unit are set at a supply portion V for dilution and pretreatment. For the items requiring the dilution or pretreatment, the dilute solution or pretreatment liquid set in, for example, the reagent storage portion B is dispensed into the reaction vessels 7 by means of the reagent dispensation transfer portion 5, and thereafter the reaction vessels 7 are transferred to the outer circumferential line 1a of the immunity reaction table 1 by means of the reaction vessel transfer portion 6B.

Samples are collected from the specimen racks supplied from the sampler S by means of the sample dispensation transfer portion 4 having sample tips fitted thereon, and such samples are dispensed into the reaction vessels 7 on the immunity reaction table 1.

During the steps described above, another reaction vessel (for measurement) 7 is set in the reaction vessel supply portion U and is transferred to the BF table (outside) 2 by means of the reaction vessel transfer portion 6B. The magnetic particle solidus carrier reagent is dispensed into the reaction vessel (for measurement) 7 transferred to the BF table 2 by means of the reagent dispensation transfer portion 5. (The one step method and other measuring method are substantially similar to those described above.)

Samples are collected from the reaction vessels (for dilution and pretreatment) 7 containing samples diluted and pretreated by means of the sample dispensation transfer portion 4, and such samples are dispensed into the reaction vessels (for measurement) 7 on the BF table 2 and the contents in the reaction vessels 7 are then agitated by the agitating mechanism 2c.

The following analyzing operations for the reaction vessels (for measurement) 7 are carried out in the similar manner to those in the two step method described above (or another method described above). The reaction vessels (for dilution and pretreatment) 7 are transferred through the reaction vessel transfer portion 6 to the reaction vessel disposing position L and disposed or thrown away.

Although the automatic analysis using two reactor vessels is explained in the above embodiment, it is possible to perform the automatic analysis including dilution and pretreatment using only one reaction vessel. For this purpose, first, a reaction vessel (for dilution and pretreatment) 7, which has been subjected to a dilution or pretreatment, is transferred from the immunity reaction table 1 to the BF table 2, and thereafter the reaction vessel is subjected to the same steps as those in the reaction vessel 7 for measurement described above with the exception of the dispensation of the sample on the BF table 2. In this manner, it is possible to perform the dilution and pretreatment with only one reaction vessel.

In order to carry out the analysis continuously for a prolonged period of time, preferably there may be provided means capable of setting a plurality of substrate bottles or means capable of supplying reaction vessels with a feeder for parts. In this case, there are further provided a plurality of tip cases having sample tips received therein and means for transferring tips from the tip cases to tip supply portion positions (where nozzles and tips are fitted with each other), such that the transportation of tip cases themselves is reduced as much as possible or eliminated, thereby enabling used tip cases to be conveniently and safely exchanged with new tip cases even in analyses continuing for a prolonged period of time.

By providing the feeder for parts, it becomes possible to add consumption articles at any time without stoppage of the apparatus. It is common to prepare an exclusive cleaning agent for nozzles. Preferably, a cleaning agent reservoir is provided, which is able to automatically dilute a concentrated cleaning agent to supply the dilute cleaning agent, thereby enabling the concentrated cleaning agent to be replenished.

Used consumption articles to be discarded are transferred by a discarding box. When the discarding box is filled with the articles to be discarded, the box is exchanged with a subsidiary tank, thereby enabling waste articles to throw away at any time. Moreover, a pump is provided to automatically discharge the waste liquor, thereby enabling continuous treatment of the waste liquor.

In the analyzing operations described above, it is assumed that the immunity reaction time or pretreatment reaction time is terminated during one rotation of the immunity reaction table 1. However, the liquid to be inspected is maintained until the immunity reaction table 1 has been rotated a plural times depending upon the performance or property of a reagent so as to permit the reaction time (including pretreatment time) to be prolonged for the number of rotations. Therefore, it becomes possible to use a reagent whose reaction time is comparatively long.

Each of tables is controlled to be at a constant temperature in a manner that the immunity reaction and the reaction for producing signals are effected under the most suitable conditions. For this purpose, each of the tables is made of a substance superior in thermal conductivity, for example, aluminum and is heated directly by heating means such as a heater or is brought into contact with another heat source. The temperature of the table is controlled at a constant by monitoring by the use of a thermistor.

In addition to the tables, the reaction vessel supply portion and the detection measurement portion may be controlled to be constant temperatures. In order to avoid any variance in temperature of liquids to be inspected during cleaning (BF operation) of the reaction vessel, the BF nozzle $2b$ may be controlled to be a constant temperature or the BF liquid may be supplied after being heated by causing it to pass through a heated portion.

In order to avoid any variance in temperature of liquids to be inspected during dispensing operation of the reagent, preferably, the reagent dispensation transfer portion 5 is controlled to be a constant temperature, or the cleaning agent for cleaning the nozzles is supplied after it has been warmed up by previously causing it to pass through a heated portion.

The operating conditions of the respective tables may be determined so as to be the most suitable conditions in layout to meet specifications of automatic analysis to be effected. For example, the table may be moved with one pitch or 180° plus one pitch per one cycle of operation. In effect, the table may be operated with a cycle commensurate with the number of ports at which reaction vessels can be set such that all the ports can be used. The respective operations of the tables may be suitably set without requiring any coincidence of operating conditions of the respective tables.

Figure 10:
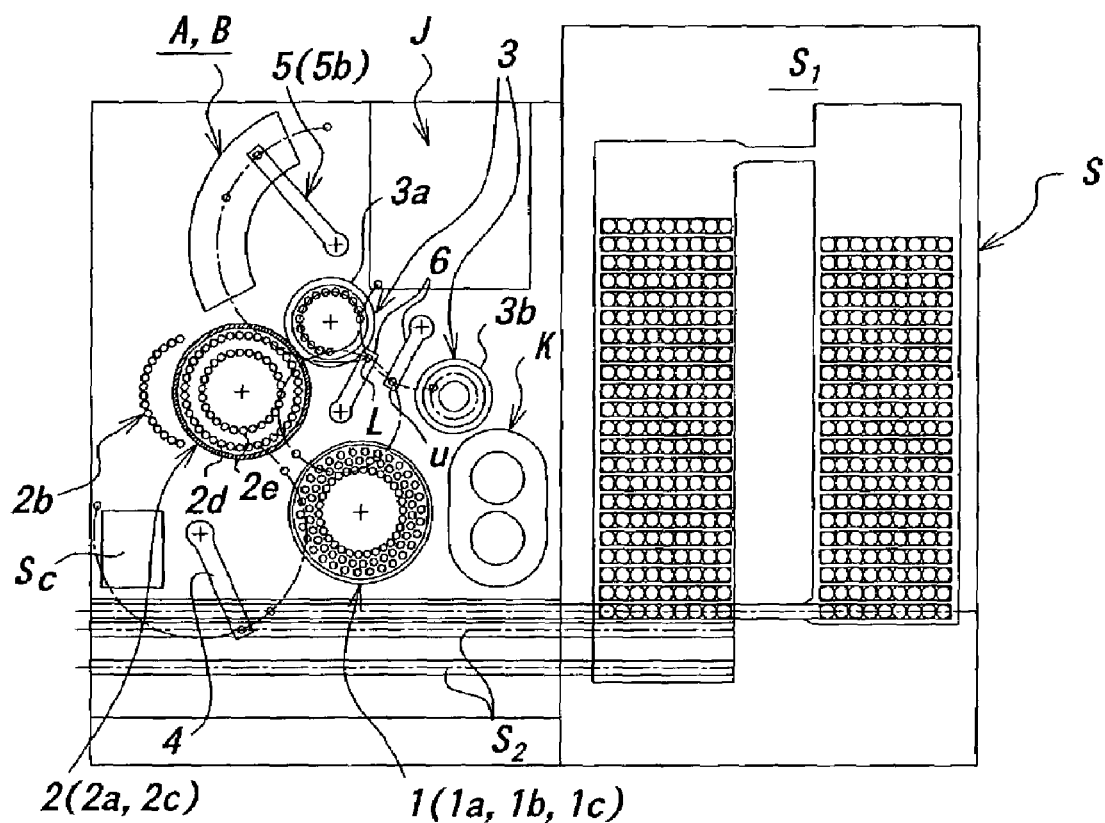
FIG. 10 is a view illustrating an automatic analyzing apparatus according to another embodiment of the invention.

FIG. 10 illustrates an analyzing apparatus having one reagent storage portion according to another embodiment of the invention. With this apparatus of the construction, the reagent storage portion may be stationary and in the form of a turn table, and the portion 5A of the reagent dispensation transfer portions 5A and 5B can be dispensed with. In this case, the apparatus can be more miniaturized.

Figure 11:
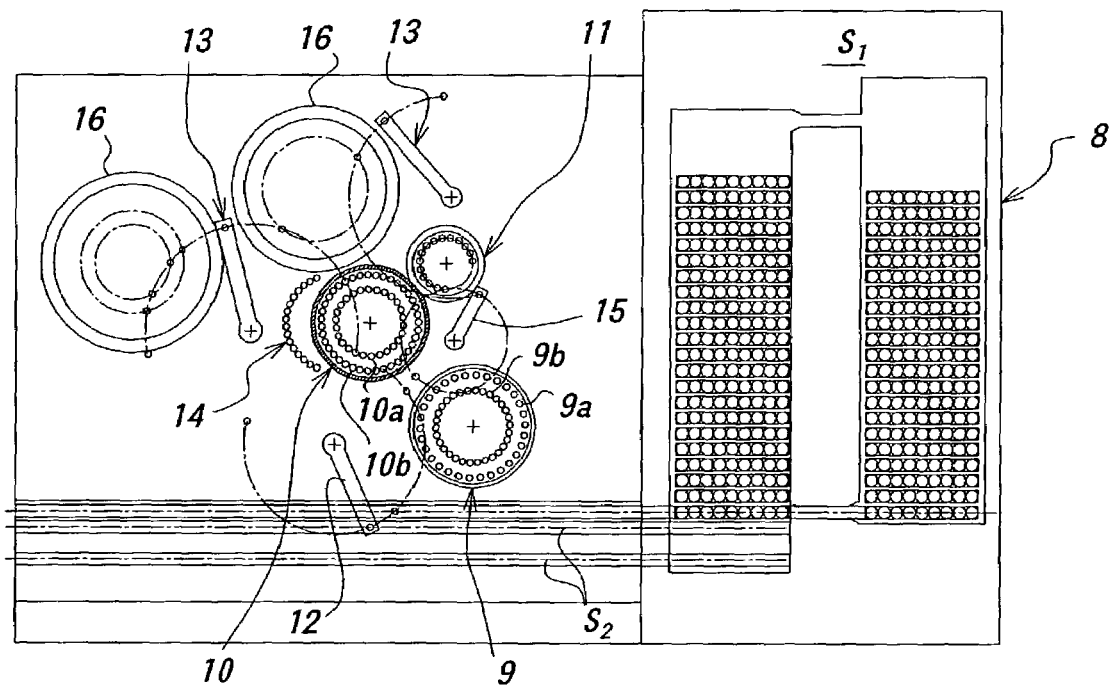
FIG. 11 is a view illustrating an automatic analyzing apparatus according to a further embodiment of the invention.
Figure 12:
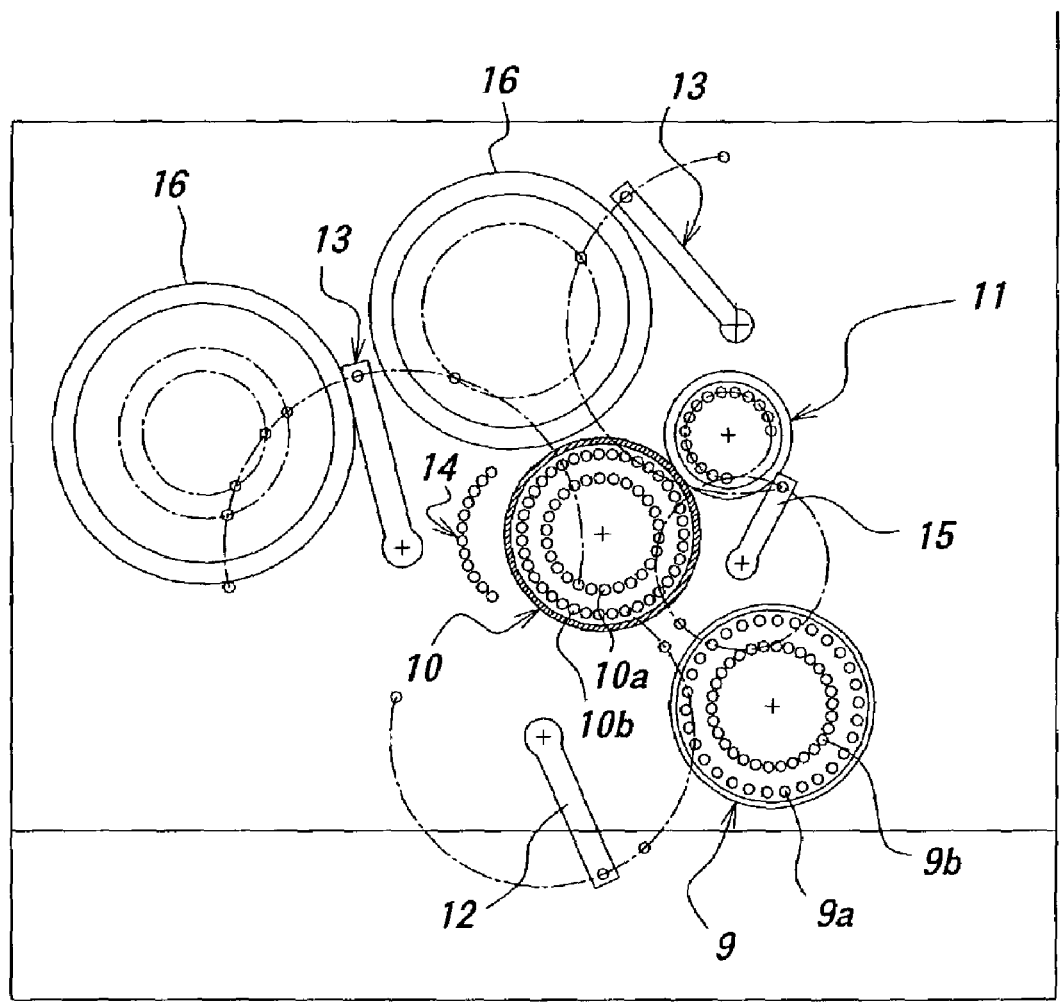
FIG. 12 is a view illustrating an important part of the automatic analyzing apparatus shown in FIG. 10.
Figure 13:
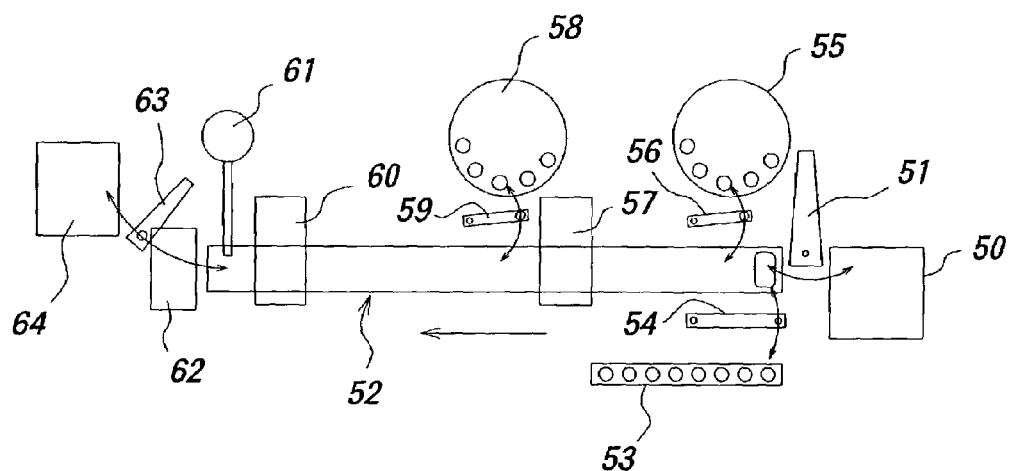
FIG. 13 is a view pictorially illustrating the construction of the automatic analyzing apparatus of the prior art.
Figure 14:
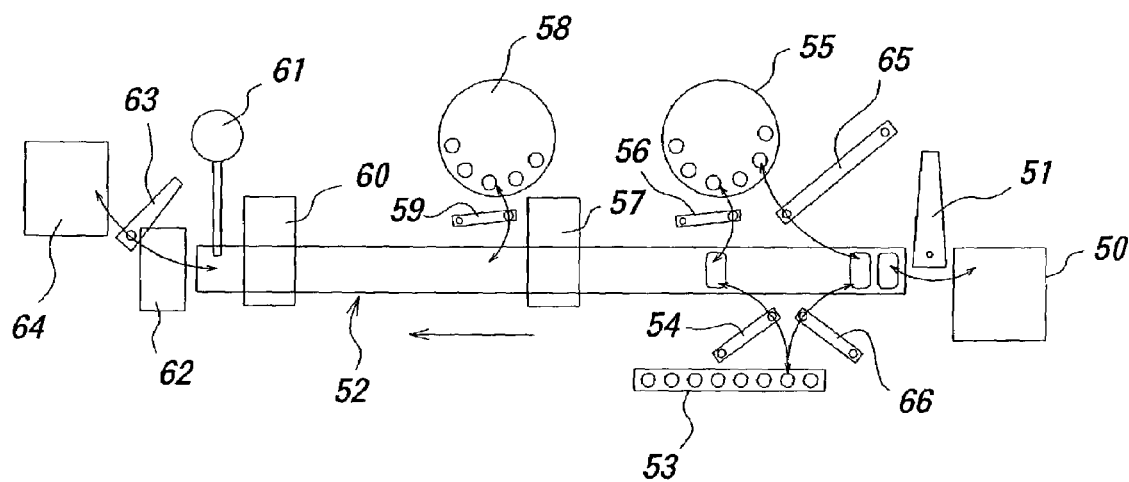
FIG. 14 is a view pictorially illustrating the construction of the automatic analyzing apparatus of the prior art having a pretreatment function.

FIGS. 11 and 12 illustrate the entire construction and an important portion of an automatic analyzing apparatus according to another embodiment of the invention applied to measurement for chemicobiological and homogeneous immunity items.

In FIGS. 11 and 12, the apparatus comprises a sampler 8, a reaction table 9, a cleaning table 10, a detecting reaction table 11, a sample dispensing nozzle 12, reagent dispensing nozzles 13, a reaction vessel cleaning nozzle 14, a reaction vessel transfer unit 15, and a reagent storage portion 16. In the analyzing apparatus constructed described above, the sampler 8 may be similar to the sampler S shown in FIG. 1.

The reaction table 9 may have a reaction line having a configuration of a double construction consisting of an outer circumferential line $9a$ for pretreatment and predilution and an inner circumferential line $9b$ for reaction of sample and first reagent.

The cleaning table 10 has cleaning nozzles for cleaning reaction vessels after completion of measurement, and all the dispensations of reagent take place in the cleaning table 10. The cleaning table 10 includes double lines, that is, on inner side a reaction vessel cleaning line $10a$ and on outer side a reagent dispensing line $10b$, thereby enabling the dispensing steps to be effected with high efficiency. The reaction vessel cleaning line $10a$ of the cleaning table 10 may be provided with reaction vessel locating positions a few times (about three times in the drawing) the reaction vessel locating positions of the dispensing line $10b$ so that the reaction vessels including reaction vessels for dilution can be cleaned at the cleaning line $10a$.

The suction and discharge agitation can be carried out by the use of the dispensing nozzles. According to the invention, however, it is preferable to employ the agitating mechanism similar to that shown in FIG. 3. The detecting reaction table 11 is provided on its reaction line with a colorimetric detector to accommodate both the rate method and end method.

The sample dispensing nozzle 12 collects specimens from the racks supplied by the sampler S and dispenses the specimens into required reaction vessels. In case of items requiring dilution and pretreatment, for example, the specimens are dispensed by the sample dispensing nozzle 12 into reaction vessels on the pretreatment and predilution lines of the reaction table 9. In a normal analysis, as described above, in the cleaning table 10 the dispensation is effected into the reaction vessels into which reagents have previously been dispensed. The sample dispensing nozzle 12 is designed to have an operating locus passing through the rack transfer portion $S_2$ of the sampler S, the reaction table 9 and a cleaning table 10. A plurality of the sample dispensing nozzles 12 are not necessarily needed according to inspection items.

The reagent dispensing nozzles 13 collect reagents from the reagent bottles arranged in the reagent storage portion 16 and dispense the reagent into required reaction vessels or into reaction vessels in which samples have not been dispensed. The reagent dispensing nozzles 13 are designed to have an operating locus passing through the reagent storage portion 16 and the cleaning table 10.

The two units of the reagent dispensing nozzle 13 are shown in the illustrated embodiment. By increasing the number of units of the nozzle 13, the collection and dispensation can be effected at a plurality of positions from the reagent storage portion 16, thereby considerably increasing the treating speed.

The reaction vessel cleaning nozzle 14 performs suction of liquids to be inspected and supply of cleaning agent and consists of a combination of a suction nozzle and a discharge nozzle. Concerning the reaction vessel transfer unit 15, similar one to the transfer portion 6 shown in FIGS. $5a$ and $5b$ may be used for the same purpose.

The reagent storage portion 16 is maintained at a constant temperature which is a comparatively lower temperature and may be in the form of a turn table arranged in coincidence with the operating locus of the reagent dispensing nozzle 13 as shown in FIG. 1 or may be arranged side by side on the operating locus of the reagent dispensing nozzles 13 as shown in FIG. 10. A plurality (two in the illustrated embodiment) of reagent storage portions 16 in the form of a turn table are arranged so that it becomes possible to dispense reagents arranged in a plurality of reagent storage portions by means of a single reagent dispensing nozzle 13.

A bottle of the reagent in the reagent storage portion 16 has a reagent code (for example, bar code) attached thereto recording the information of the reagent (for example, a lot, effective term, measurement line information or the like). The reagent storage portion 16 is provided with means for reading these codes, such as a bar code reader, image reader, magnetic reader or the like so that the information read from the information code together with positional information of the reagent storage portion 16 which has been set, set date and the like is transmitted to a data processor and memorized.

The automatic analysis using the apparatus shown in FIGS. 11 and 12 is carried out in the following manner. First, a reaction vessel is cleaned in the inner line of the cleaning table 10 and a first reagent is dispensed into the reaction vessel by means of the reagent dispensing nozzle 13. Thereafter, a sample is dispensed into the reaction vessel by means of the sample dispensing nozzle 12, and the content in the reaction vessel is agitated by an agitating mechanism in successive manner.

After agitation, the reaction vessel is transferred to the inner line of the reaction table 9 by means of the reaction vessel transfer unit 15. The reaction vessel is kept at this location for a constant reaction time and then transferred to the outer line of the cleaning table 10 by means of the reaction vessel transfer unit 15. If required, a second reagent and a third reagent are dispensed into the reaction vessel on the cleaning table 10 and then the content in the reaction vessel is agitated.

Thereafter, the reaction vessel is moved to the detecting reaction table 11 by means of the reaction vessel transfer unit 15, where the reaction condition of the content in the reaction vessel is detected by the rate method or end method using a colorimeter. After the detection, the reaction vessel is transferred to the inner circumferential line of the cleaning table 10 by means of the reaction vessel transfer unit 15 and cleaned.

The analysis requiring dilution and pretreatment is carried out in the following manner. When a first reagent is dispensed into a cleaned reaction vessel, simultaneously a dilute solution or pretreatment liquid set in the reagent storage portion 16 is dispensed into the reaction vessel by means of the reagent dispensing nozzle 13, and then a sample is dispensed into the reaction vessel by means of the sample dispensing nozzle 12. Thereafter, the content in the reaction vessel is agitated by the agitating mechanism.

After the agitation, the reaction vessel is transferred to the outer circumferential line of the reaction table 9 by means of the reaction vessel transfer unit 15. When the reaction vessel whose content has been subjected to the dilution or pretreatment is transferred onto the operating locus of the sample dispensing nozzle 12, a reaction vessel for test reaction is assigned to the reaction vessel in a manner such that a sample liquid which has been diluted or pretreated can be dispensed into the reaction vessel at the sample dispersion timing in normal operation.

The vessel assigned as a reaction vessel is transferred to the inner circumferential line of the cleaning table 10 where the vessel is cleaned and a first reagent is dispensed into the vessel. Thereafter, a sample liquid that has been diluted or pretreated is dispensed at the sample dispersing timing into the vessel from the reaction vessel (whose content has been diluted or pretreated) arranged on the outer circumferential line of the reaction table 9.

Thereafter, the reaction vessel is subjected to the steps the same as those in the normal operation. The reaction vessel used for dilution or pretreatment is returned to the cleaning table 10 by means of the reaction vessel transfer unit 15 to be cleaned.

FIGS. 11 and 12 illustrate the apparatus for measuring and analyzing chemicobiological items, which, however, is included in the apparatus shown in FIGS. 1 and 2 for measuring and analyzing the immunity items. With the apparatus shown in FIGS. 1 and 2, by suitably controlling the transferring of the reaction vessels, both the chemicobiological (homogeneous) items and immunity (heterogeneous) items can be analyzed or measured only by one apparatus. The present invention should not be limited to these apparatuses.

The automatic analyzing apparatus according to the invention is also applicable to an analyzing apparatus for genetical inspections, and therefore it is also possible to construct an automatic analyzing system by suitably combining genetical analyzing items with the above mentioned chemicobiological analyzing items and immunity analyzing items.

While the invention has been particularly shown and described with reference to preferred embodiments thereof, it will be understood by those skilled in the art that the foregoing and other changes in form and details can be made therein without departing from the spirit and scope of the invention.

What is claimed is:

1. An automatic analyzing apparatus for measuring an object substance in a specimen, said apparatus comprising:
 a reaction portion for causing said substance of the specimen and a reagent commensurate thereto to react on each other,
 a detecting portion for detecting a signal or reaction condition from said reagent for measuring the object substance, and
 a cleaning portion for removing said substance of the specimen or unreacted substance in said reagent or cleaning the reacted liquids which have completed the reaction, and said reaction, detecting and cleaning portions being independently arranged in a single frame, and wherein said reaction, detecting and cleaning portions are in the form of turn tables, respectively,
 a transfer portion being provided for transferring reaction vessels in succession between said reaction, detecting and cleaning portions to perform said measurement of the object substance;
 wherein said detecting portion is arranged to be divided into a detecting reaction portion and a detecting measurement portion, respectively, and the transfer portion is adapted to transfer the reaction vessels between the detecting reaction portion and the detecting measurement portion.

2. The automatic analyzing apparatus as set forth in claim 1, wherein said reaction portion includes a pretreatment and a dilution portion for the specimen.

3. The automatic analyzing apparatus as set forth in claim 1, wherein said cleaning portion includes magnetically collecting means for magnetically collecting magnetic particles used as solidus carriers and agitating means for dispersing the magnetic particles.

* * * * *